United States Patent [19]

Razavi

[11] Patent Number: 5,117,020

[45] Date of Patent: May 26, 1992

[54] PROCESS FOR THE PREPARATION OF METALLOCENES

[75] Inventor: Abbas Razavi, Paturages, Belgium

[73] Assignee: Fina Research, S.A., Feluy, Belgium

[21] Appl. No.: 603,059

[22] Filed: Oct. 25, 1990

[30] Foreign Application Priority Data

Oct. 30, 1989 [EP] European Pat. Off. ............ 89870164

[51] Int. Cl.$^5$ .......................... C07F 17/00; C07F 9/00; C07F 11/00
[52] U.S. Cl. ........................................ 556/43; 556/53; 556/58
[58] Field of Search ............................. 556/43, 53, 58

[56] References Cited

U.S. PATENT DOCUMENTS

| | | | |
|---|---|---|---|
| 4,851,598 | 6/1990 | Miya et al. | 502/117 |
| 4,892,851 | 1/1990 | Ewen et al. | 502/104 |
| 4,931,417 | 7/1989 | Rosenblum et al. | 585/25 |
| 5,036,034 | 7/1991 | Ewen | 502/117 |

FOREIGN PATENT DOCUMENTS 0284707 10/1988 European Pat. Off. .

OTHER PUBLICATIONS

"Di aryl Bis—(Cyclopentadienyl)—titanium compounds"; Summers et al., J. of Am. Chem. Soc., vol. 77, No. 13, pp. 3604–3606 (Jul., 1955).

Primary Examiner—Jose G. Dees
Assistant Examiner—Porfirio Nazario
Attorney, Agent, or Firm—Jim D. Wheelington; John K. Abokhair; M. Norwood Cheairs

[57] ABSTRACT

A transition metal salt and powder of the solid reaction product of the ligand with an alkyllithium are reacted at room temperature in a non-polar hydrocarbon. The metallocene thus obtained has a sufficient purity for subsequent use as catalyst for the polymerization of olefins without further purification.

10 Claims, 4 Drawing Sheets

PROCESS FOR THE PREPARATION OF METALLOCENES

BACKGROUND OF INVENTION

1. Field of Invention

The present invention relates to the preparation of metallocene compounds. More particularly, the present invention relates to a new process for the reaction of metal cations with cyclopentadienyl-type anions to form metallocenes.

2. Description of Prior Art

Metallocenes are being increasingly used as catalysts for the polymerization of olefins. Ewen and Razavi have recently disclosed that metallocene catalysts can be tailored to control the stereospecificity of polypropylene (JACS, 110, 6255-6, 1988). However, such control may be largely dependent on the purity of the catalysts.

Generally, the preparation of metallocene compounds consists of forming and isolating the cyclopentadienyl or substituted cyclopentadienyl ligand(s), which are reacted with a halogenated or alkylated transition metal compound to form a complex which is then purified.

European Patent Application No. 89870079.4 discloses two methods for the preparation of metallocenes.

In method A, n-butyllithium is added to a solution of the ligand in tetrahydrofuran (THF), after which metal chloride in THF is added with vigorous stirring. After refluxing, removal of the solvent leaves a mixture of LiCl and a red solid. However, this method gives metallocenes which are extremely-air and moisture-sensitive, and which are in addition somewhat impure so that they generally have to be purified by either pentane extraction, fractional recrystallization, or chromatography. The final complex nevertheless contains some THF, coordinated to the metal.

In method B, methylene chloride is used as a non-coordinating solvent. The reaction product of n-butyllithium with the ligand is isolated and dissolved in methylene chloride at the same temperature is added, and the mixture is allowed to warm slowly to room temperature before filtering off LiCl. However, this method gives a solution of an impure metallocene in methylene chloride, which must be recrystallized and washed. Further, this method requires the use of very low temperatures.

There is thus a need in the art for a method for preparing metallocene compounds that would not have the above drawbacks.

SUMMARY OF INVENTION

It is an object of this invention to provide a process for the preparation of metallocenes having a sufficient purity for subsequent use as catalysts for the polymerization of olefins, without need for further purification.

Another object of the invention is to provide a process for the preparation of metallocenes that would not require working at very low temperatures.

Still another object of the invention is to provide a process for the preparation of metallocenes with a high yield.

Accordingly, the process of the invention for the preparation of metallocenes comprises the steps of:

(i) reacting a transition metal salt and powder of the solid reaction product produced by reacting a ligand with an alkyllithium in a non-polar hydrocarbon liquid; and (ii) recovering a solid mixture of lithium salt and metallocene.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Figure 1:
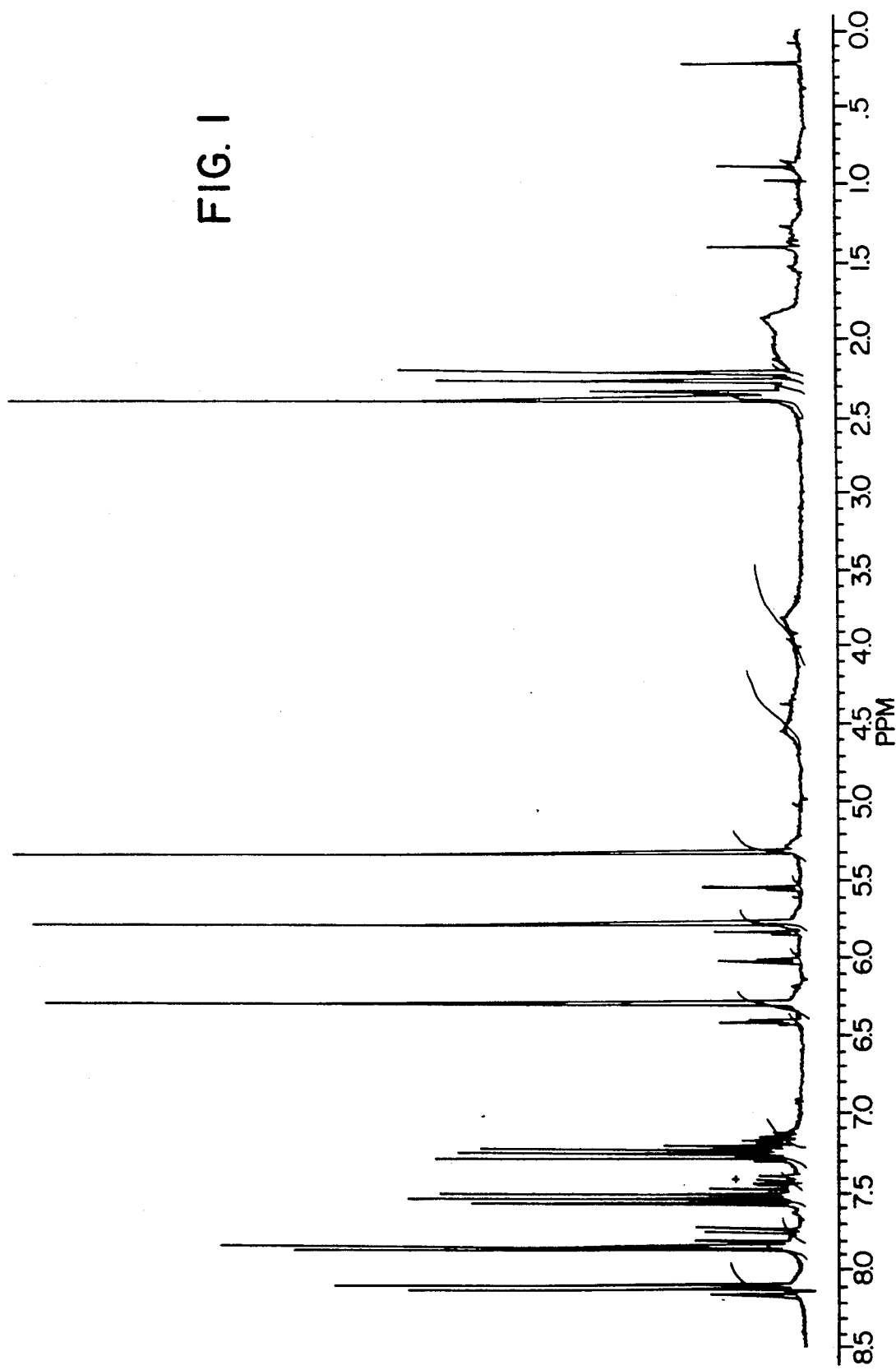
FIG. 1 represents the $^{13}C$—NMR spectrum of a metallocene prepared by the process of the invention.
Figure 2:
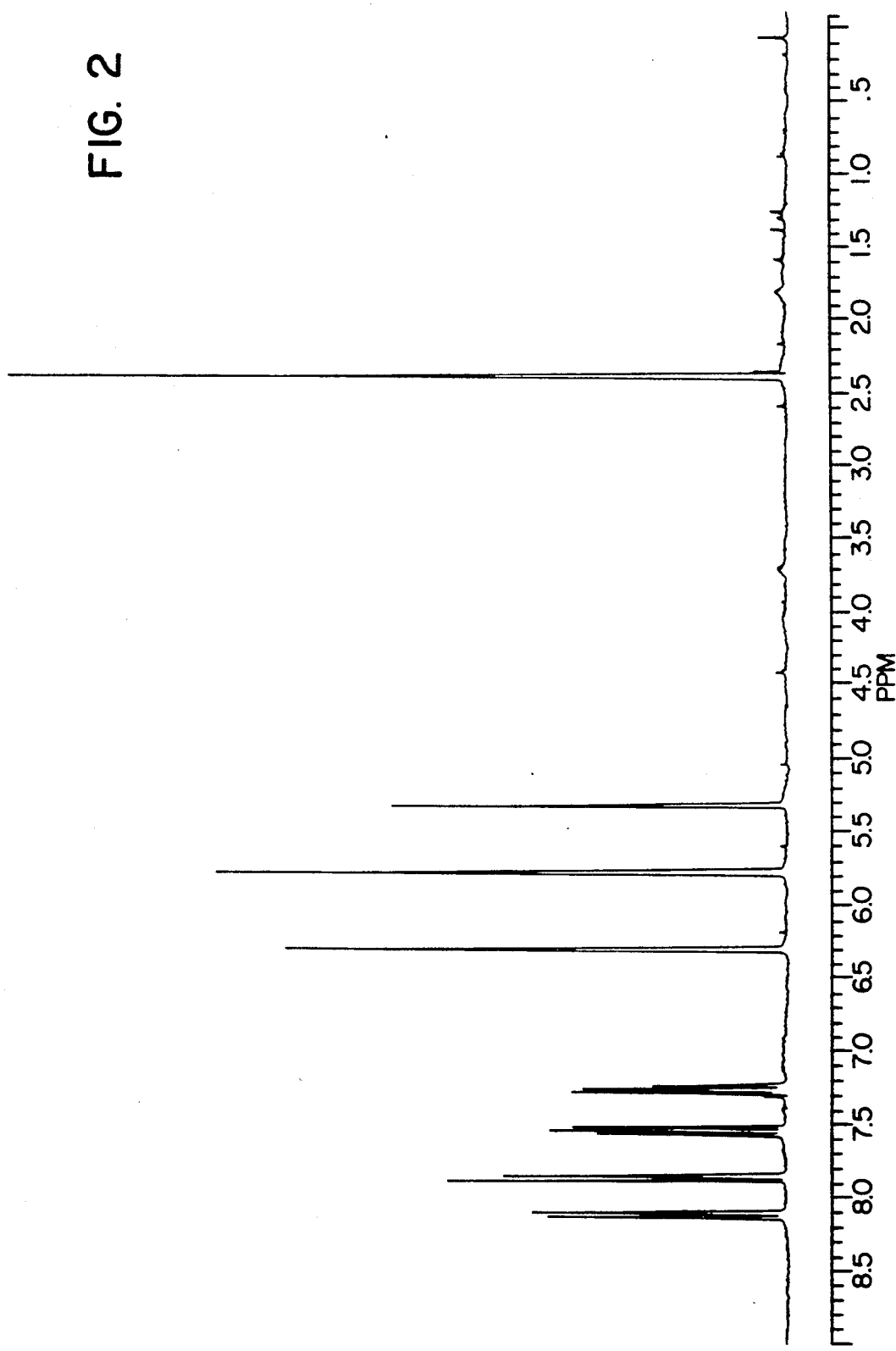
FIG. 2 represents the $^{13}C$—NMR spectrum of a metallocene obtained by a conventional process.
Figure 3:
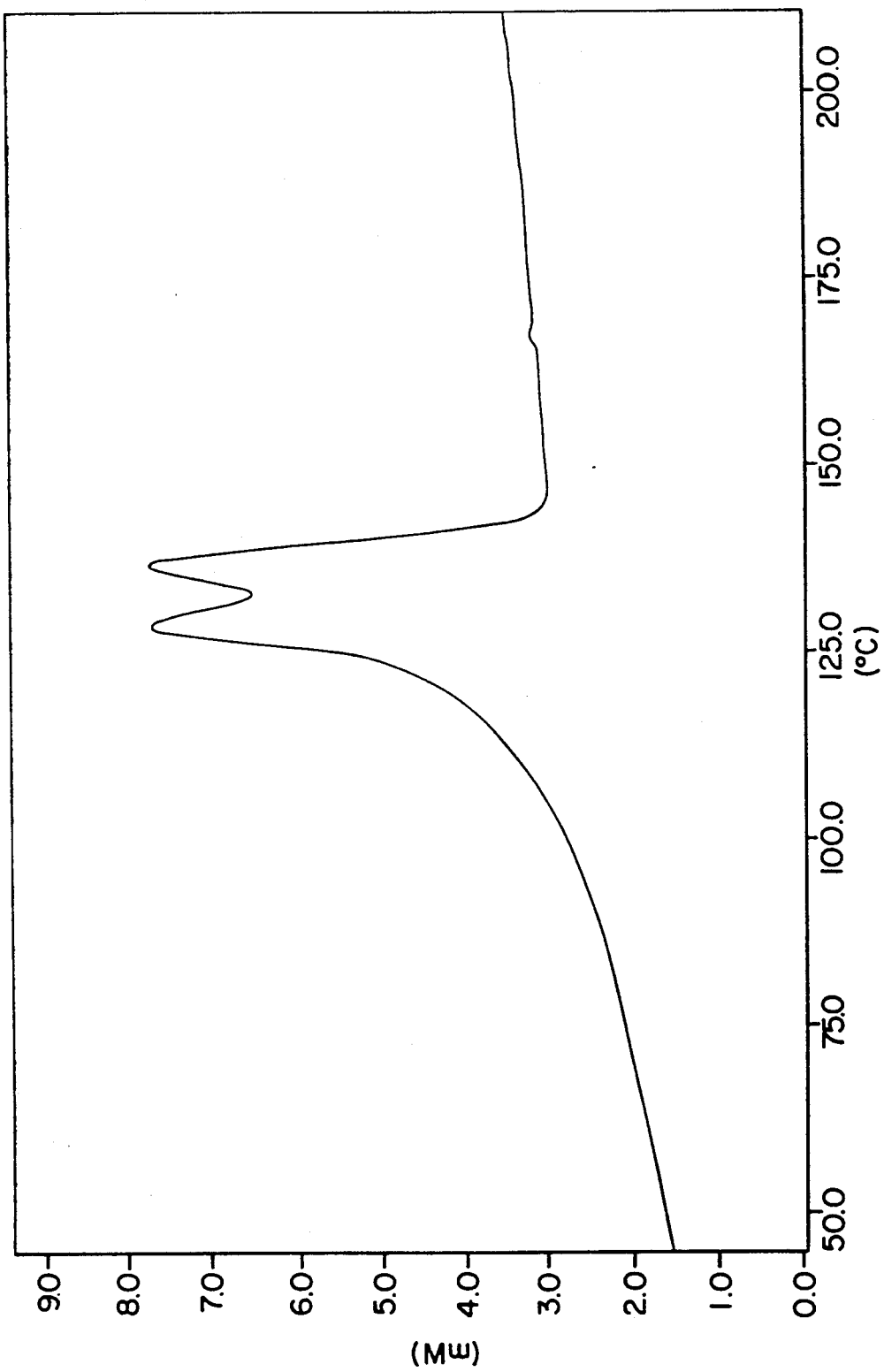
FIG. 3 represents the differential scanning colorimetry of the syndiotactic polypropylene obtained with a metallocene catalyst prepared by the process of the invention. The heat flow (expressed in °C)
Figure 4:
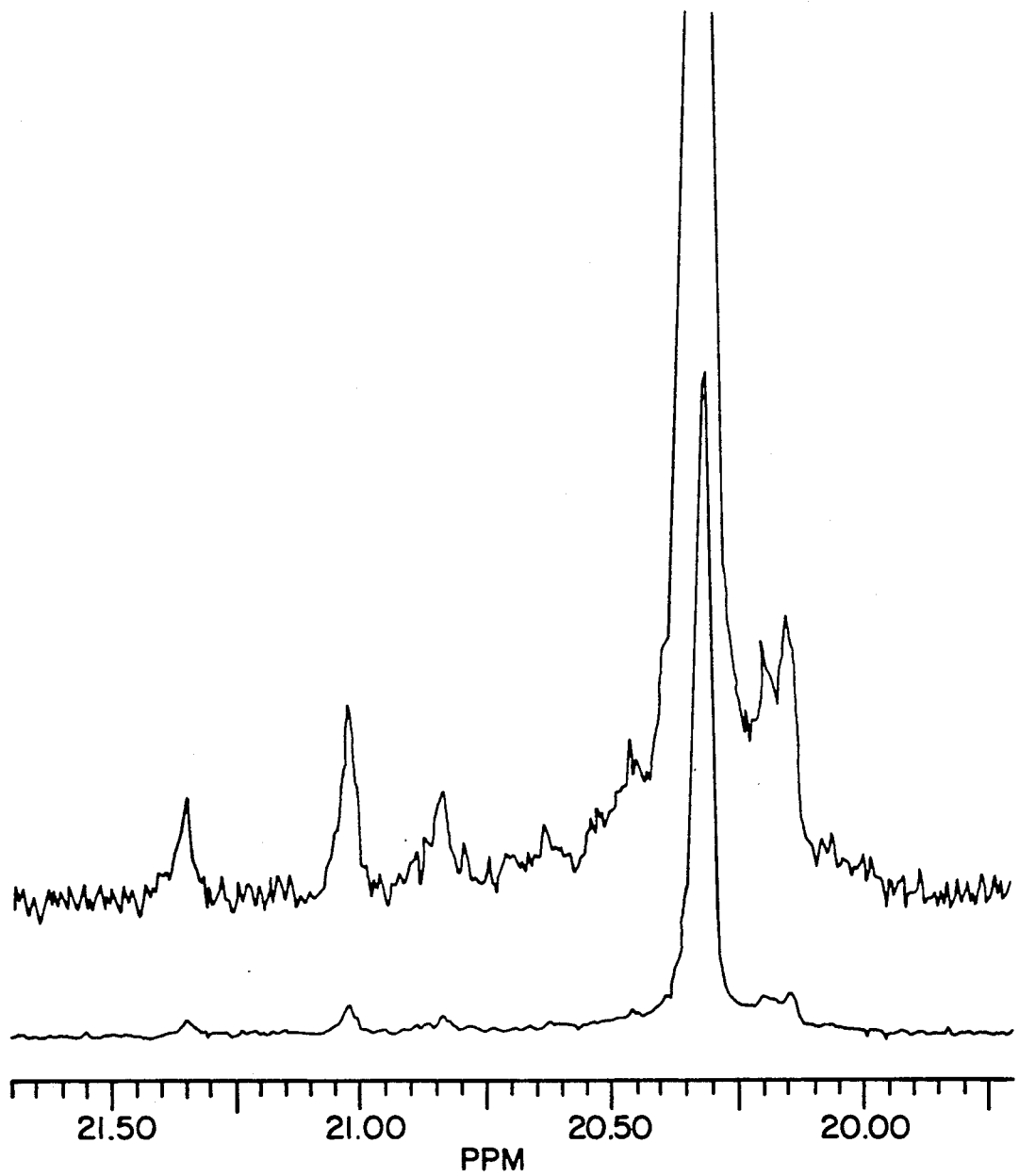
FIG. 4 represents the $^{13}C$—NMR spectrum of syndiotactic polypropylene obtained with a metallocene prepared by the process of the invention.

The process of the invention is applicable to a large variety of metallocene syntheses. As examples of ligands, there may be cited cyclopentadiene, substituted cyclopentadienes, and bridged dicyclopentadienes wherein each cyclopentadiene may be equal or different and may be substituted or not. Substituted cyclopentadienes may have either one substituent or several substituents which may be the same or different. As substituents, there may be cited hydrocarbyl radicals having from 1 to 20 carbon. Exemplary hydrocarbyl radicals include methyl, ethyl, propyl, isopropyl, butyl, isobutyl, amyl, isoamyl, hexyl, heptyl, octyl, nonyl, decyl, cetyl, phenyl, and the like. Other hydrocarbyl radicals useful in the present catalysts include other alkyl, aryl, alkenyl, alkylaryl or arylalkyl radicals. Further, substituents comprise hydrocarbyl radicals attached to a single carbon atom in the cyclopentadiene ring as well as radicals that are bonded to two carbon atoms in the ring.

The ligand may be prepared using various processes known in the art, depending on the selection of the specific ring substituents and bridge, if any.

The reaction of the ligand with an alkyllithium is known in the art; it is generally carried out by dropwise addition of an alkyllithium solution in a solution of the ligand. Methyl lithium and n-butyllithium are most often used, as are stoichiometric ratios of the reactants. The solid reaction product may be recovered by complete evaporation of the solvent. Depending on the evaporation conditions, said product may have to be reduced to a fine powder, e.g. by grinding in a mortar.

As transition metal salt, there is generally used a halide or halide derivative. If said salt is solid, it should preferably be in the form of a fine powder, else the solid should be finely powdered, e.g. by grinding in a mortar.

When the catalyst is to be used for the polymerization of olefins, the metal is usually selected from Groups 4, 5 or 6 (formerly known as groups IVb, Vb, VIb) and more particularly selected from the group consisting if Ti, Zr, Hf, V and Cr, although other transition metals could be contemplated for that or for other uses of the catalyst.

As examples of non-polar hydrocarbon liquids, there may be cited the alkanes having 3 to 12 carbon atoms. Preferred liquids are the alkanes having 4 to 6 carbon atoms, the most preferred being pentane because of its ease of removal. Indeed, although higher alkanes like decane could be used as non-polar hydrocarbon liquid, their complete removal in the next step would require washing with a lighter liquid alkane like pentane.

While this procedure is entirely new in the field of metallocene preparation, where those skilled in the art would use as reaction medium a liquid reacting with the lithiated ligand, the applicant has found that the reaction between the powders proceeds relatively quickly to completion even though at least the lithiated ligand powder is substantially insoluble in the non-polar hydrocarbon liquid. This is even surprising when the transition metal salt is also substantially insoluble in the said liquid, because one skilled in the art would believe that the reaction would not proceed.

The temperature of the mixture during the reaction step can be adjusted within a very wide range, at least between $-20°$ C. and $+100°$ C., preferably between $0°$ and $60°$ C., room temperature (about $25°$ C.) being most preferred for obvious reasons. As one of ordinary skill in the art knows, lowering the temperature will require a longer reaction time, while increasing the temperature may allow to shorten the reaction time. As a general approach, overnight stirring of the mixture at room temperature gives a substantially total reaction. Slight heating of the mixture (e.g. refluxing of a pentane suspension) may allow to reduce the reaction time down to a few hours.

The reaction pressure is usually atmospheric, although operation with liquid butane or propane may require higher pressures.

As everyone knows, dry (moisture-free) and oxygen-free conditions are required for this type of reaction and for the storage of the metallocenes.

After completion of the reaction step, a solid mixture of lithium salt and metallocene may be recovered, usually be decantation or filtration, and washed with fresh non-polar hydrocarbon liquid, preferably with an easily removed alkane like pentane.

Yields attainable with the process of the invention are very high, typically above 90%. As comparison, it may be indicated that methods previously known using methylene chloride only give yields of the order of 40%.

The metallocene obtained is very pure, except for the presence of a lithium salt, and generally does not require a purification step. If required, selective extraction of the metallocene may be used. When metallocenes are used as catalysts for the polymerization of olefins, the presence of small amounts of a pure lithium salt like LiCl does not appear to have any significant effect on the activity of the catalyst.

The invention will now be described further by means of the following examples which should not be construed as limiting the invention in any way, and by means of FIGS. 1-4:

EXAMPLE 1

A. Preparation of a Ligand 41.5 GRAMS (0.25 mol) of fluorene were dissolved in 350 ml of tetrahydrofuran (THF) in a 500 ml round bottom flask equipped with a side arm and dropping funnel with pressure equalizer.

0.25 mol of methyllithium ($CH_3Li$) Were added dropwise as a 1.6M solution in ether. Stirring of the orange-red solution was continued for three hours.

After gas evolution had ceased, 100 ml of THF containing 26.5 g (0.25 mol) of 6,6-dimethylfulvene was added dropwise to the solution. Stirring of the red solution was continued overnight.

The resulting solution was then washed with 200 ml of a saturated ammonium chloride aqueous solution, then with water.

After evaporation of the solvents, a yellow powder was recovered on the surface of the water. Recrystallization by dissolving the yellow powder in 500 ml chloroform and addition of excess methanol at $2°$ C. yielded a white powder of 2,2-isopropenyl fluorene cyclopentadiene.

B. Reaction of the Ligand With Alkyllithium 10 g (0.0368 mol) of the ligand were dissolved in 200 ml THF in a 500 ml round bottom flask equipped with a side dropping funnel.

0.0736 mol of methyllithium were added dropwise as a 1.6M solution in ether. Stirring of the red solution was continued for three hours.

After gas evolution had ceased, the solvents were evaporated at $40°$ C., leaving a finely powdered yellow-orange product after about 2 hours.

C. Reaction of the Metal Salt With the Lithiated Ligand

The yellow-orange powder was mixed with 8.57 g of $ZrCl_4$ powder. Evidence of a slight reaction could be a slight change of the color towards red.

300 ml of pentane were then added as reaction medium, and the resulting suspension was stirred overnight at room temperature ($23°$ C.), under atmospheric pressure.

The supernatant solution was then removed, and the red powder was washed with pentane and dried. The $^{13}C$—NMR spectrum of the red powder was substantially identical to that of the same metallocene when prepared using methylene chloride at low temperature (see comparative example).

This process yielded 17.49 g of red powder, corresponding to 100% yield (calculated values = 15.93 g metallocene +1.56 g LiCl). FIG. 1 shows the $^{13}C$—NMR spectrum of that powder. The spectrum is identical to that of the same compound obtained by using methylene chloride as reaction medium (FIG. 2), except for small peaks which correspond to isopropenyl cyclopentadienyl fluorenyl zirconium dichloride wherein one or two chloride atoms are replaced by $CH_3$ groups; such metallocenes are as active as the dichloride catalyst for the polymerization of olefins.

D. Polymerization of Propylene 2 mg of the mixture obtained hereabove (containing 1.82 mg of metallocene and 0.18 mg LiCl) was dissolved in 2.5 ml of a 10 wt % solution of methylalumoxane in toluene, giving a bright violet solution. A 250 ml autoclave vessel was filled with 100 ml liquid propylene and thermostated at $20°$ C. while agitating. The catalyst solution was injected through a septum in a valve void on top of the 250 ml vessel and flushed into the 250 ml vessel with 100 ml liquid propylene.

After 3 minutes, the interconnecting valve between the two reactors was opened and the content of the vessel was flushed with 0.9 liter propylene into the 4.5 liter autoclave previously filled with another 0.9 liter of liquid propylene. The whole was left polymerizing for 1 hour keeping the temperature constant at 60° C., after which reaction was stopped by venting off unreacted monomer and the reactor was opened to air. The fluff was dried under reduced pressure at 50° C. overnight. 173 g of a nice free flowing powder of spherical particles of syndiotactic polypropylene were obtained. The bulk density was measured according to ASTM-D-1898 and the melt flow index according to ASTM-D-1238 (5 kg/190° C.). Differential scanning colorimetry was used to determine the melting points (see FIG. 3) and heat of crystallization of the polymer. $^{13}$C—NMR was used to determine the tacticity of the polypropylene (FIG. 4); referring to the description of European Patent Application no. 89870079.4, few mistakes were observed, among which meso triads were predominant over meso dyads. The results are indicated in Tables 1 and 2.

TABLE 1

| | | Syndiotactic Polypropylene | |
|---|---|---|---|
| | Units | Example | Comparative Examples |
| Yield | g | 173 | 185 |
| Calculated | g/g catalyst | 96100 | 89800 |
| Bulk Density | g/cm$^3$ | 0.14 | 0.16 |
| Melt Index | g/10 min | 12.6 | 12.6 |
| Melting Points | °C. | 128.4 | 128 |
| | °C. | 136.8 | 137 |
| Heat of Crystallization | J/g | −32.98 | −37 |
| Tacticity | rrrr | 80% | 79.5% |
| | r | 92% | 93.3% |

TABLE 2

| $^{13}$C-NMR of Syndiotactic Polypropylene | | | |
|---|---|---|---|
| Sequence | Shift | Surface | % |
| mmmm | 21.71 | 0.00 | 0.00 |
| mmmr | 21.46 | 0.00 | 0.00 |
| rmmr | 21.27 | 4.65 | 2.30 |
| mmrr | 20.95 | 7.35 | 3.63 |
| rmrr + mrmm | 20.77 | 6.03 | 2.98 |
| mrmr | 20.60 | 6.61 | 3.27 |
| rrrr | 20.25 | 161.58 | 79.85 |
| mrr | 20.10 | 13.14 | 6.49 |

COMPARATIVE EXAMPLE

A. Preparation of a Ligand 2,2-isopropenyl fluorene cyclopentadiene was prepared according to the procedure described in Example 1.

B. Reaction of the Ligand With the Alkyllithium

The procedure of Example 1 was followed.

C. Reaction of the Metal With the Lithiated Ligand 0.025 mol of the ligand dilithium derivative was dissolved in 125 ml of cold methylene chloride at −78° C.

A slurry of 0.025 mol of ZrCl$_4$ in 125 ml of cold methylene chloride was poured in the flask containing the lithiated ligand solution. The mixture was stirred during two hours at −78° C., allowed to warm slowly to room temperature (23° C.) and stirred for a additional 12 hours.

Insoluble white LiCl was filtered off before crystallizing a red powder by cooling the red solution to −20° C. for 12 hours.

After decantation, the red crystalline powder was washed several times methylene chloride at −20° C. and isolated by removing the solvent under vacuum.

This process yielded 4.1 grams (0.0095 mol) of metallocene. i.e. a yield of about 38%.

D. Polymerization of Propylene

Under the same conditions as in example 1, except that 2.06 mg of catalyst were used and that the propylene pressure was of 2.76 MPa, syndiotactic polypropylene was obtained with yield and properties substantially identical to those of example 1 (Table 1).

EXAMPLE 2

A. Preparation of the Ligand 2,2-isopropenyl fluorene cyclopentadiene was prepared according to the procedure of example 1.

B. Reaction of the Ligand With the Alkyllithium

The procedure of example 1 was followed.

C. Reaction of the Metal Salt With the Lithiated Ligand

The yellow-orange lithiated ligand powder was mixed at room temperature with a 10 wt % solution of an equimolar amount of TiCl$_4$ in pentane.

The mixture was stirred for one hour, still at room temperature, filtered and washed with pentane to recover a brown powder containing LiCl and 2,2-isopropenyl fluorenyl cyclopentadienyl titanium dichloride and a small amount of LiCl.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States is:

1. Process for the preparation of metallocenes, comprising the steps of
   (i) reacting in a non-polar hydrocarbon liquid a transition metal salt and powder of solid reaction product produced by reacting a ligand with an alkyllithium; and
   (ii) recovering a solid mixture of lithium salt and metallocene; wherein the ligand is selected from the group consisting of cyclopentadiene, substituted cyclopentadienes, and bridged dicyclopentadienes wherein each cyclopentadiene may be equal or different and may be substituted or not.

2. Process according to claim 1, wherein the transition metal is selected from groups 4, 5 and 6.

3. Process according to claim 2, wherein the transition metal is selected from the group consisting of Ti, Zr, Hf, V and Cr.

4. Process according to claim 1, wherein the transition metal salt is a halide.

5. Process according to claim 1, wherein the non-polar hydrocarbon liquid is an alkane having 3 to 12 carbon atoms.

6. Process according to claim 5, wherein the non-polar hydrocarbon liquid is an alkane having 4 to 6 carbon atoms.

7. Process according to claim 6, wherein the non-polar hydrocarbon liquid is pentane.

8. Process according to claim 1, wherein step (i) is carried out at a temperature of from −20° C. to +100° C.

9. Process according to claim 9, wherein step (i) is carried out at a temperature of from 0° C. to 60° C.

10. Process according to claim 9, wherein step (i) is carried out at a temperature of about 25° C.

* * * * *